(12) United States Patent
Raven et al.

(10) Patent No.: US 7,635,348 B2
(45) Date of Patent: Dec. 22, 2009

(54) CONTAINER FOR MEDICAMENT AUTOMATIC INJECTOR AND AUTOMATIC INJECTOR ADAPTED THEREFOR

(75) Inventors: Sophie Rebecca Raven, Cambs (GB); Matthew Egerton Young, Cambs (GB); Paul Greenhalgh, Bucks (GB); Stephen Pilip Kirkwood, Beds (GB); Colin James Mathews, Huntington (GB); Joseph William Daintrey, Herts (GB); John G. Wilmot, Mount Airy, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 525 days.

(21) Appl. No.: 10/978,827

(22) Filed: Nov. 2, 2004

(65) Prior Publication Data

US 2005/0148933 A1    Jul. 7, 2005

Related U.S. Application Data

(60) Provisional application No. 60/516,733, filed on Nov. 4, 2003, provisional application No. 60/517,910, filed on Nov. 7, 2003.

(51) Int. Cl.
*A61M 5/00* (2006.01)

(52) U.S. Cl. .................. 604/111; 604/187; 604/192; 604/197; 604/193; 604/228; 604/229; 604/131; 604/134; 604/135

(58) Field of Classification Search ............... 604/181, 604/182, 187, 189, 192, 197, 228, 229, 234, 604/131, 135, 136, 93.1, 111
See application file for complete search history.

(56) References Cited

U.S. PATENT DOCUMENTS 1,506,429 A    8/1924    Kahn et al.

(Continued)

FOREIGN PATENT DOCUMENTS

DE    19959507 A1    6/2000

(Continued)

*Primary Examiner*—Nicholas D Lucchesi
*Assistant Examiner*—Quynh-Nhu H Vu
(74) *Attorney, Agent, or Firm*—Jones Day; Garry J. Tuma

(57) ABSTRACT

Containers for automatic injectors and automatic injectors adapted for those containers are disclosed. The containers include structures adapted to retain and, optionally, cripple the needle of the automatic injector when the automatic injector is inserted into the container after use. Depending on the embodiment, an indicator may be included, either as part of the container or as part of the automatic injector, to indicate whether or not the automatic injector has been used. If the indicator is provided as a part of the automatic injector, a corresponding portion of the container may be formed of a light permeable material. The container may also include features, such as an eyelet over the closed end, designed to cushion the automatic injector. Cushioning and shock absorbing features may also be provided inside the container. A clip is also disclosed. The clip is designed to attach two or more containers together.

50 Claims, 11 Drawing Sheets

U.S. PATENT DOCUMENTS

| | | | |
|---|---|---|---|
| 1,711,594 A * | 5/1929 | Gillespie | 206/365 |
| 1,718,701 A | 6/1929 | O'Sullivan | |
| 1,838,825 A | 12/1931 | Goldstein | |
| 2,400,722 A | 5/1946 | Swan | |
| 3,363,497 A * | 1/1968 | Thompson | 84/380 C |
| 3,367,486 A | 2/1968 | Larson et al. | |
| 4,188,950 A | 2/1980 | Wardlaw | |
| 4,332,323 A | 6/1982 | Reenstierna | |
| 4,634,428 A | 1/1987 | Cuu | |
| 4,716,710 A | 1/1988 | Galy et al. | |
| 4,728,320 A | 3/1988 | Chen | |
| 4,728,321 A | 3/1988 | Chen | |
| 4,735,311 A | 4/1988 | Lowe et al. | |
| 4,872,552 A | 10/1989 | Unger | |
| 4,877,132 A | 10/1989 | Makris et al. | |
| 5,002,533 A | 3/1991 | Jullien | |
| 5,015,234 A | 5/1991 | Jullien | |
| 5,074,848 A | 12/1991 | Burt et al. | |
| 5,080,651 A | 1/1992 | Jullien | |
| 5,084,027 A | 1/1992 | Bernard | |
| 5,104,375 A | 4/1992 | Wolf et al. | |
| 5,137,516 A | 8/1992 | Rand et al. | |
| 5,156,267 A | 10/1992 | Yates, Jr. et al. | |
| 5,161,681 A | 11/1992 | Kemp et al. | |
| 5,172,808 A | 12/1992 | Bruno | |
| 5,188,600 A | 2/1993 | Jullien | |
| 5,232,454 A | 8/1993 | Hollister | |
| 5,232,455 A | 8/1993 | Hollister | |
| 5,358,489 A * | 10/1994 | Wyrick | 604/136 |
| 5,391,151 A * | 2/1995 | Wilmot | 604/139 |
| 5,417,326 A | 5/1995 | Winer | |
| 5,519,931 A | 5/1996 | Reich | |
| 5,522,503 A | 6/1996 | Halbich | |
| 5,566,828 A | 10/1996 | Claes et al. | |
| 5,695,472 A | 12/1997 | Wyrick | |
| 5,918,443 A | 7/1999 | Phillips | |
| 5,941,854 A * | 8/1999 | Bhitiyakul | 604/168.01 |
| 5,950,827 A | 9/1999 | Odom et al. | |
| 5,980,495 A | 11/1999 | Heinz et al. | |
| 6,001,082 A * | 12/1999 | Dair et al. | 604/207 |
| 6,026,959 A | 2/2000 | Lowe | |
| 6,102,893 A | 8/2000 | Aneas | |
| 6,155,420 A | 12/2000 | Phillips | |
| 6,183,439 B1 | 2/2001 | Nakajima | |
| 6,210,369 B1 * | 4/2001 | Wilmot et al. | 604/157 |
| 6,217,558 B1 * | 4/2001 | Zadini et al. | 604/187 |
| 6,241,709 B1 | 6/2001 | Bechtold et al. | |
| 6,405,912 B2 | 6/2002 | Giannou | |
| 6,454,746 B1 * | 9/2002 | Bydlon et al. | 604/227 |
| 6,576,918 B1 | 6/2003 | Fu et al. | |
| 6,595,362 B2 | 7/2003 | Penney et al. | |
| 6,641,560 B1 * | 11/2003 | Bechtold et al. | 604/136 |
| 6,641,561 B1 | 11/2003 | Hill et al. | |
| 6,702,785 B1 | 3/2004 | Collins | |
| 6,767,336 B1 * | 7/2004 | Kaplan | 604/136 |
| 6,793,646 B1 * | 9/2004 | Giambattista et al. | 604/90 |
| 2001/0054631 A1 | 12/2001 | Giannou | |
| 2002/0049407 A1 | 4/2002 | Hill et al. | |
| 2002/0050462 A1 | 5/2002 | Penney et al. | |
| 2003/0132128 A1 | 7/2003 | Mazur | |
| 2004/0069667 A1 | 4/2004 | Tomellini et al. | |
| 2004/0236289 A1 * | 11/2004 | Ferguson et al. | 604/263 |

FOREIGN PATENT DOCUMENTS

| | | |
|---|---|---|
| EP | 0 634 140 A1 | 1/1995 |
| WO | WO 98/55168 | 12/1998 |
| WO | WO 99/37343 | 7/1999 |
| WO | WO 01/78806 A1 | 10/2001 |

* cited by examiner

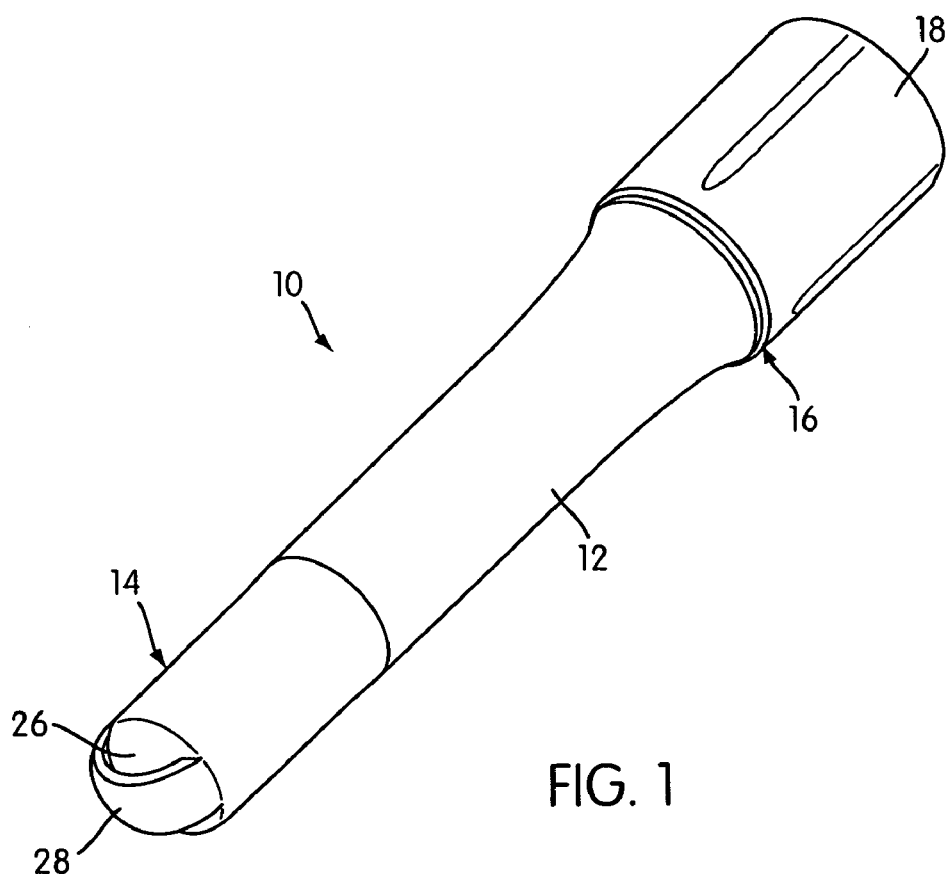
FIG. 1
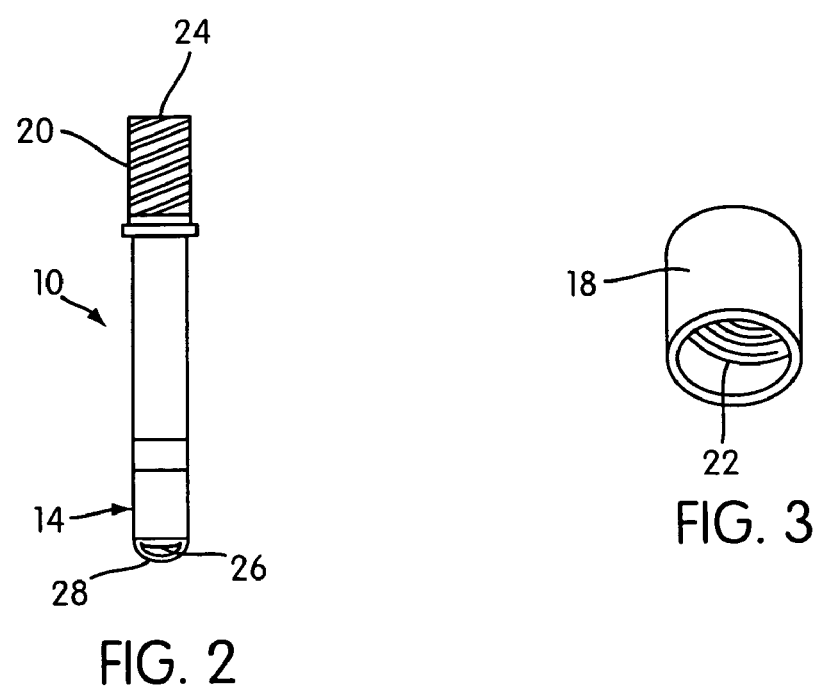
FIG. 2
FIG. 3

CONTAINER FOR MEDICAMENT AUTOMATIC INJECTOR AND AUTOMATIC INJECTOR ADAPTED THEREFOR

CROSS REFERENCE TO RELATED APPLICATIONS

This application relates to and claims priority to U.S. Provisional Patent Application No. 60/516,733, filed on Nov. 4, 2003 and U.S. Provisional Patent Application No. 60/517,910, filed on Nov. 7, 2003. The disclosures of each are incorporated specifically herein by reference.

BACKGROUND OF THE INVENTION

1. Field of the Invention

The present invention relates to containers for carrying and storing medicament automatic injectors before and after use of the injectors. The present invention also relates to a clip for carrying one or more of the containers.

2. Description of Related Art

A medicament automatic injector is a device designed to allow a user to self-administer a pre-measured dose of a medicament composition subcutaneously or intramuscularly, usually in an emergency situation. Automatic injectors are used, for example, to treat anaphylactic (severe allergic) reactions and to administer antidotes for certain poisons, such as chemical nerve agents. One of the most well known automatic injectors is the automatic injector sold under the name EPIPEN® by Meridian Medical Technologies, Inc. (Columbia, Md., United States), which delivers epinephrine.

A typical automatic injector has a housing, inside of which is a cartridge. The cartridge has one or several chambers containing medicament compositions or components thereof and is adapted to be attached to a needle assembly. The automatic injector can house a premixed dosage of medicament, liquid dosages that are mixed prior to injection, or a solid medicament that is dissolved in a liquid transport solution prior to injection. The housing carries an actuation assembly with a stored energy source, for example, a compressed spring. Activation of the actuation assembly causes a sequence of movements, the medicament compound is subsequently forced through the needle and into the user. If the automatic injector is of the type designed to carry several components of the medicament composition in separate, sealed compartments, structure may be included that forces the components to mix when the actuation assembly is activated. When the automatic injector has been used, a needle typically extends from the housing.

Automatic injectors are typically packaged in containers to keep them clean and protect them from damage. However, the typical automatic injector container is not designed to house the automatic injector after use.

SUMMARY OF THE INVENTION

One aspect of the invention relates to an automatic injector package. The automatic injector package comprises an automatic injector, a container, and indicia. The automatic injector includes a housing, a cartridge assembly carried within the housing, a needle assembly operatively associated with the cartridge assembly, and an actuation assembly carried by the housing. The actuation assembly includes a stored energy source and a drive assembly driven by the stored energy source. The drive assembly is operatively associated with the cartridge assembly and the needle assembly to expel a medicament from the cartridge and through the needle assembly upon activation of the automatic injector. The container is constructed and arranged to receive the automatic injector before and after use. At least a portion of the container is formed from a light permeable material. The indicia are provided on at least one of the housing and the container and are visible by a user when the automatic injector has been placed into the container after use. The indicia point to an indicating portion that indicates that the automatic injector has been used.

Another aspect of the invention relates to a container for an automatic injector. The container comprises an open end and a closed end opposite the open end. A cap is constructed and arranged to releasably engage the open end so as to releasably close the open end. A needle retainer is mounted within the container proximate to the closed end. A position of the needle retainer relative to the closed end is such that the distance between the needle retainer and the closed end is shorter than the length of a protruding needle of the automatic injector.

A further aspect of the invention relates to a method for using an automatic injector including a cartridge and needle assembly coupled to an actuation assembly including a stored energy source. The method comprises storing the automatic injector in a container in an unused condition. The automatic injector is used, resulting in the extension of a needle. The automatic injector is returned to the container after use, thereby causing the automatic injector to be retained in the container by engagement of the extended needle with retaining structure provided within the container.

Other aspects and advantages of the invention will become apparent from the following description.

BRIEF DESCRIPTION OF THE DRAWINGS

The invention will be described with reference to the following drawing figures, in which like numerals represent like structures, and in which:

FIG. 1 is a perspective view of an automatic injector container according to an embodiment of the present invention;

FIG. 2 is a side elevational view of the container of FIG. 1 with the container's cap removed;

FIG. 3 is a perspective view of the cap;

DETAILED DESCRIPTION

Figure 4:
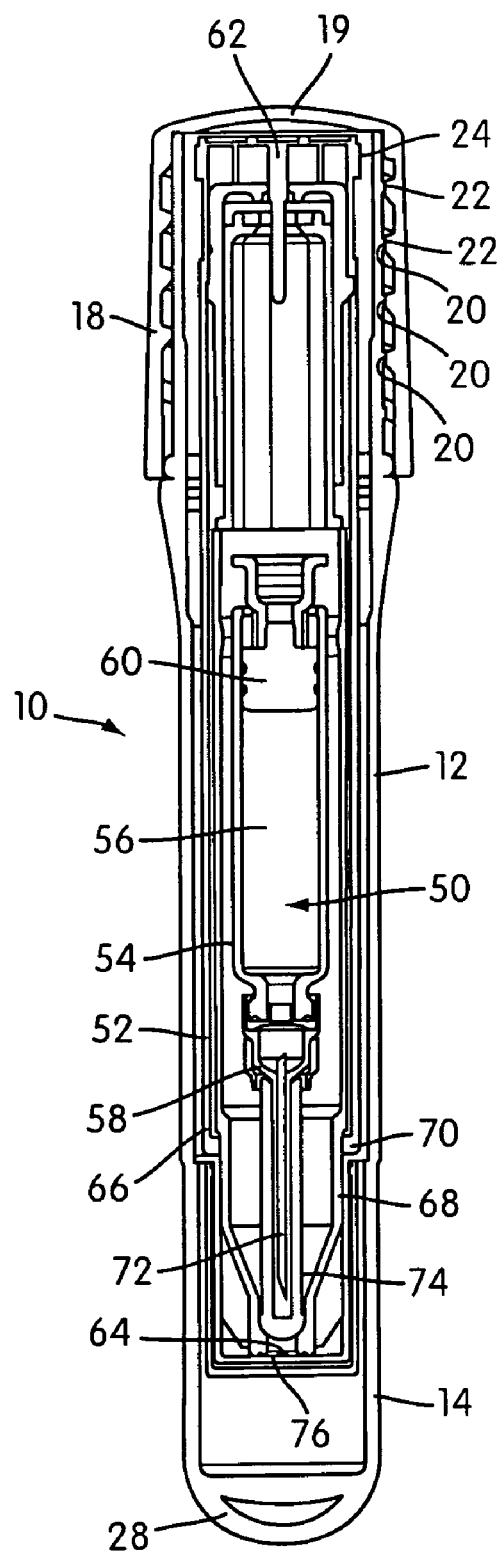
FIG. 4 is a longitudinal cross-sectional view of the container of FIG. 1, illustrating an unused automatic injector within the container.

FIG. 1 is a perspective view of a container, generally indicated at 10, according to one embodiment of the invention. The container 10 is generally cylindrical and is sized to contain an automatic injector (not shown in FIG. 1). The container 10 may be used with any type or variety of automatic injector known in the art.

Typically, the container 10 would be distributed with an automatic injector inside, and would thus serve, at least in part, as product packaging for the automatic injector. Accordingly, the central exterior surface 12 of the container 10 provides space for product labeling, usage directions, or other necessary indicia. Such labeling and indicia may be printed on labels and attached to the exterior surface 12, or they may be formed or printed on the central exterior surface 12 during the manufacture of the container 10.

In general, the container 10 may be made of a conventional plastic material such as polypropylene (PP). However, the container 10, or portions thereof, may also be made of more penetration resistant materials, such as poly(ethylene terephthalate) (PET), as will be explained below in more detail.

The container 10 has a closed needle-receiving end, generally indicated at 14, and an open end 16 opposite the needle-receiving end 14. The opening 24 in the open end 20 is of sufficient size to allow an automatic injector to be removed and replaced. In FIG. 1, the open end 16 is covered by a removable cap 18. FIG. 2 is a side elevational view of the container 10 with the cap 18 removed. FIG. 3 is a perspective view of the cap 18 in isolation. As shown, the open end 16 of the container 10 includes threads 20 that engage corresponding threads 22 on the interior of the cap 18 to releasably engage the cap 18 and container 10. Two sets of six individual non-contiguous helical threads 20 are provided on container 10, and the cap includes a corresponding set of conventional contiguous threads 22. This arrangement allows the cap 18 to start threading onto the container 10 when placed on the container 10 in a number of initial positions, and thus making it easier to thread the cap 18 on the container 10. However, a conventional set of threads may be used on the cap 18 and container 10. The exterior surface of the cap 18 may also be provided with a number of contoured portions spaced around its circumference in order to provide the user with a better grip when opening or closing the cap 18.

The container 10 is designed to house an automatic injector such that its needle-bearing end extends toward the needle-receiving end 14 of the container 10. The needle-receiving end 14 of the container 10 may have a smaller diameter than the rest of the container 10, depending on the diameter of the automatic injector that it is designed to accommodate, so as to encourage users to insert the automatic injector in the proper orientation. As shown in FIG. 1, the container 10 of the illustrated embodiment has a gradual taper, from more narrow toward the needle-receiving end 14 to broader near the cap 18. That taper corresponds to the contours of one type of automatic injector; many other contours are possible.

In particular, although the container 10 is designed to house an automatic injector with the needle-bearing end of the automatic injector facing the needle-receiving end 14 of the container 10, it is possible that the automatic injector may be placed in the container, accidentally or deliberately, such that the needle-bearing end of the automatic injector faces the cap 18. For that reason, the cap 18 is preferably made of a material of sufficient thickness, durability, and penetration resistance such that if the automatic injector were to be accidentally activated with the needle-bearing end facing the cap 18, the protruding needle would not penetrate the cap 18. Alternatively, one wall of the cap 18, such as the top wall, indicated by reference numeral 19 in FIG. 4, may be particularly thickened or may be provided with a "pad" of penetration resistant material, either plastic or metal, secured to an inward surface thereof.

The material of which the needle-receiving end 14 is made is at least partially translucent and, in some embodiments, may be fully transparent. In other embodiments, the needle-receiving end 14 may be translucent, partially translucent, or opaque, with particular portions that are fully or partially transparent. The entire container 10 may also be made of a translucent or transparent material. This feature and its utility will be described in more detail below. Regardless of the degree of light permeability of the container 10, the cap 18, or any portions thereof, the container 10 and cap 18 may be capable of blocking or absorbing ultraviolet (UV) light. For example, a UV-absorbing agent could be added to the polymer mix from which the container 10 is formed. Many such UV-absorbing agents are known in the polymer and molding arts. UV blocking or absorbing capability helps to ensure that the medicament within the automatic injector is not compromised by exposure to UV light, even if the container 10 is significantly light permeable.

The bottom 26 of the needle-receiving end 14 has a shock-absorbing eyelet 28. The eyelet 28 takes the form of an arc of material that extends across the bottom 26 of the needle-receiving end 14. The eyelet 28 acts as a shock absorber to absorb at least some of the force if the container 10 is dropped and the bottom 26 of the needle-receiving end 14 impacts another surface. The eyelet 28 would also allow a user to attach a carrying strap, so that the container may be conveniently carried. At the peak of its arc, the eyelet 28 may provide from about 1 mm to about 5 mm of clearance for the attachment of a strap. In other embodiments of the invention, there may be significant clearance between the eyelet 28 and the bottom 26.

In the embodiment shown in FIG. 1, the eyelet 28 covers approximately one-third of the bottom 26 of the needle-receiving end 14. In other embodiments, the eyelet 28 may cover from about 10% to substantially the entirety of the bottom 26 of the needle-receiving end 14. If the eyelet 28 covers only a small portion of the bottom 26 of the needle-receiving end 14, it may provide less effective shock absorption if the container 10 impacts off-center. The eyelet 28 may have a thickness of from about 0.5 mm to about 2 mm, which may vary along its arc.

FIG. 4 is a longitudinal cross-sectional view of the container 10 showing an automatic injector 50 installed therein. The automatic injector 50 illustrated in FIG. 4 has a single chamber and is designed to contain and inject a single component liquid medicament composition. However, the container 10 may also be used with two component wet/wet mixing automatic injectors, as well as two component wet/dry mixing automatic injectors, and any other type of automatic injector known in the art.

The automatic injector 50 is shown schematically in FIG. 4 and certain features have been omitted for clarity of illustration, because the workings of the automatic injector 50 are not critical to the functioning of this embodiment of the container 10. Full details of operation for automatic injectors such as automatic injector 50 may be found in commonly assigned U.S. Pat. Nos. 5,391,151 and 6,210,369, the contents of which are incorporated by reference herein. The automatic injector 50 has an outer housing 52 and a cartridge 54 disposed within the outer housing 52. The cartridge 54 includes a medicament storage compartment 56, an attached needle assembly 58, and a plunger 60 at the top of the medicament storage compartment 56. Depending on the type of automatic injector 50, the cartridge 54 may include one or two compartments, so as to accommodate medications having a wet component and a dry component (so-called "wet/dry automatic injectors") or a wet component and another wet component (so-called "wet/wet automatic injectors"). Descriptions of several suitable types of wet/dry automatic injectors can be found in commonly-assigned U.S. Pat. Nos. 6,641,561 and 6,770,052. The entire contents of those applications are incorporated by reference herein in their entirety.

The automatic injector 50 also includes an actuation assembly, only portions of which are shown in FIG. 4. Typically, a stored energy source (not shown in FIG. 4), such as a compressed spring, would be carried in the space above the plunger 60. A safety cap 62 prevents the stored energy source from releasing and activating the device. The precise manner of activation of the automatic injector 50 is not critical to the container 10; however, in a typical automatic injector 50, the safety cap 62 would be removed and the needle end 64 of the automatic injector 50 would be pressed against an administration site (e.g., the user's thigh), causing a relative movement of upper 66 and lower 68 portions of the housing 52 that causes the stored energy source to deploy and activate the automatic injector 50. (As shown, the upper portion 66 of the housing 52 includes an inwardly extending shoulder 70 against which the lower portion 68 of the housing bears.) Once the automatic injector is activated, the stored energy source propels the needle 72 through its protective sleeve 74 and the bottom 76 of the housing 52 and subsequently causes the plunger 60 to move downward, causing the medicament compound in the cartridge 54 to be dispensed through the needle 72. In most automatic injectors, internal spring force exerted against the needle 72 prevents the needle 72 from being retracted back into the housing 52 once it has been used.

FIG. 4 illustrates the position of the automatic injector 50 within the container 10 prior to use. As shown, the automatic injector 50 is completely within the container 10 and the container 10 is slightly longer than the automatic injector 50. Therefore, when the user removes the cap 18, he or she will have to tip the container 10 to remove the automatic injector 50 from it. This is advantageous because if the automatic injector 50 did protrude from the container 10, the user might try to remove it from the container 10 by tugging on or near the safety cap 62, which might cause the safety cap 62 to come loose and could ultimately result in the premature or unintended activation of the automatic injector 50.

However, the difference in length between the container 10 and the automatic injector 50 is most desirably the smallest length difference between the two that will prevent the user from accidentally removing the safety cap 62. That difference may be no more than a few millimeters. In general, the container 10 should be as small as possible, so that it can be conveniently and consistently carried by a user. If the container 10 is too large, the user may not be inclined to carry it, in which case the automatic injector 50 may not be available when it is needed.

Figure 5A:
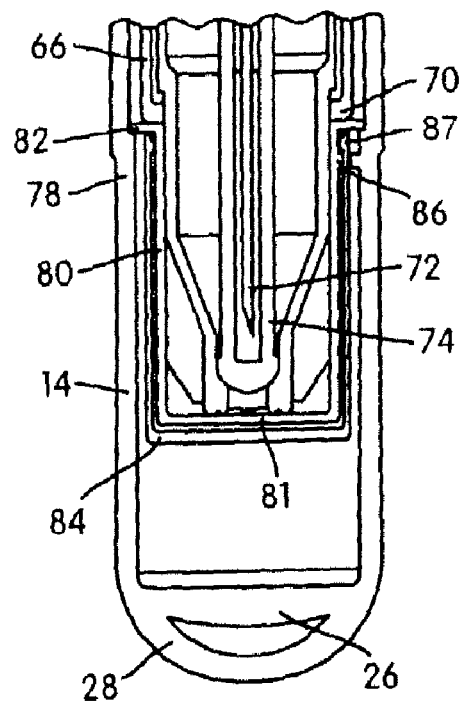
FIG. 5A is a longitudinal cross-sectional view of a portion of the container similar to the view of FIG. 4, illustrating the administration end of the automatic injector within the container prior to use.

FIG. 5A is a longitudinal cross-sectional view of a portion of the automatic injector 50, showing its "administration end" within the container 10. The interior of the container 10 has a small inwardly extending circumferential shoulder or shelf 78 formed at the top of the needle-receiving end 14 of the container 10. An indicator sleeve 80 has an outwardly extending lip 82 that rests on the shelf 78. The indicator sleeve 80 is formed of a brightly colored material that can be penetrated by the needle 72 (e.g. red plastic). In the position illustrated in FIG. 5A, the indicator sleeve 80 is covered by a cover sleeve 84, which surrounds and covers the indicator sleeve 80. The indicator sleeve 80 includes a prong or series of prongs 86 that are engaged by corresponding clips 87 on the end of the cover sleeve 84 to retain the cover sleeve 84 in the position illustrated in FIG. 5A. To some extent, the indicator sleeve 80 and cover sleeve 84 also cushion the automatic injector 50 against shock and impact.

When the user needs to use the automatic injector 50, he or she removes the cap 18 from the container 10, removes the automatic injector 50 from the container 10 as was described above, and then uses the automatic injector 50 in accordance with the manufacturer's instructions. Once the automatic injector 50 is used, the user replaces the automatic injector 50 in the container 10, inserting the automatic injector 50 such that the needle 72 is oriented toward the needle-receiving end 14 of the container 10. If the automatic injector 50 is difficult to re-insert, the user may place the cap 18 on the container 10 and turn the cap 18 toward engagement with the container 10. As the user turns the cap 18, the torque applied to the cap 18 will cause an axial force to be exerted on the automatic injector 50, forcing it into the container 10. The cap 18 may thus provide the user with a significant mechanical advantage if used to "seat" the used automatic injector 50 within the container 10 in this manner.

Figure 5B:
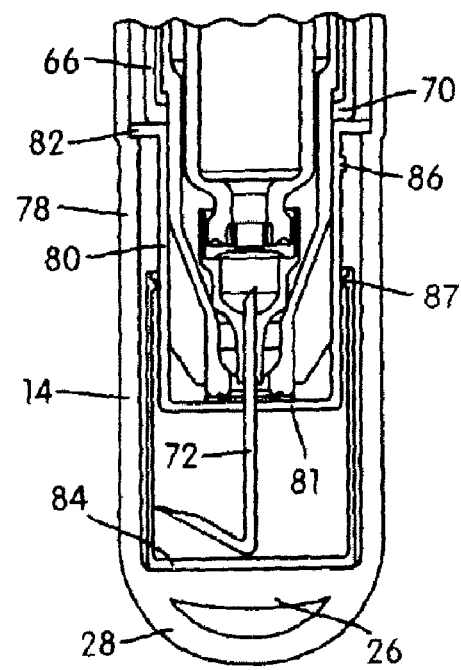
FIG. 5B is a longitudinal cross-sectional view similar to that of FIG. 5A, illustrating the administration end of the automatic injector after the automatic injector has been used and returned to the container.

As the needle 72 enters the needle-receiving end 14 of the container 10, the motion of the needle 72 causes a series of movements, which may result in the position shown in FIG. 5B. Specifically, as the needle 72 is moved into the container, it penetrates the bottom of the indicator sleeve 80, disengages the cover sleeve 84 from the indicator sleeve 80, and drives the cover sleeve 84 downward, toward the bottom of the container 10.

Figure 6A:
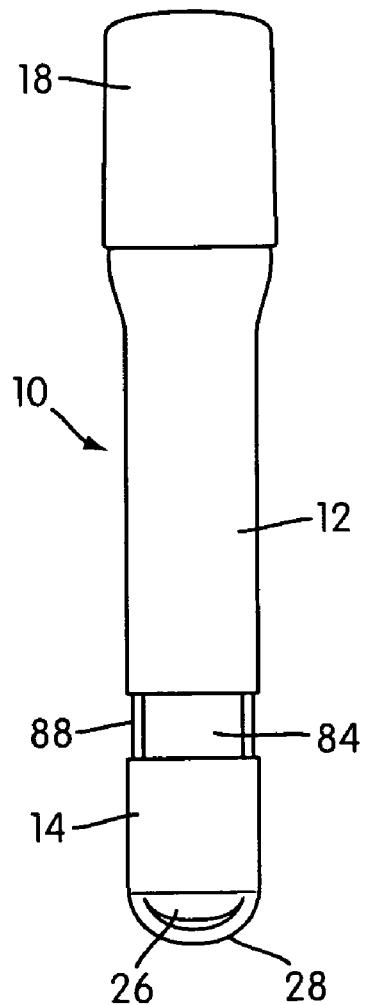
FIG. 6A is a perspective view of the exterior of the container with the automatic injector in the position illustrated in FIG. 5A.
Figure 6B:
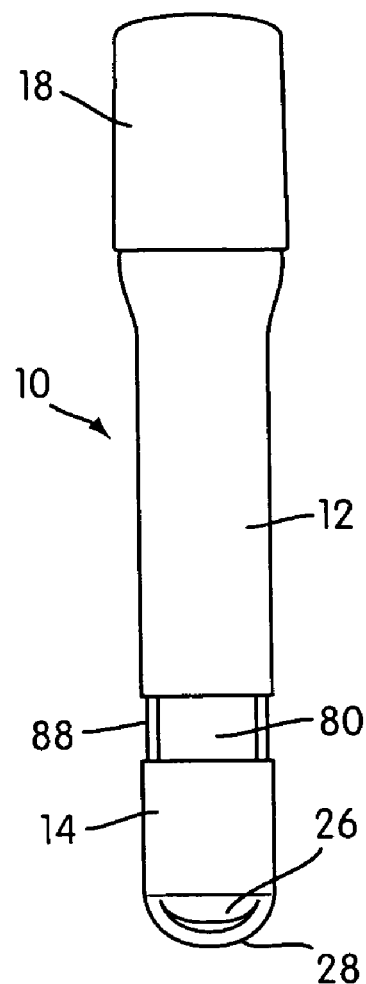
FIG. 6B is a perspective view of the exterior of the container with the automatic injector in the used position illustrated in FIG. 5B, showing a used injector indicator flag visible from the exterior of the container.

When the cover sleeve 84 is in the downward position, the indicator sleeve 80 is exposed. Because the needle-receiving portion 14 of the container 10 is at least partially translucent, the indicator sleeve 80 can be seen from the outside of the container 10. Accordingly, a user can determine, merely by looking at the outside of the container 10, whether or not the automatic injector 50 inside the container 10 has been used. FIGS. 6A and 6B are perspective views of the container 10 before and after the used automatic injector 50 has been replaced in the container 10, respectively. In FIG. 6B, the indicator sleeve 80 is clearly visible through a translucent window 88 in the needle-receiving portion 14, whereas in FIG. 6A, only the uncolored cover sleeve 84 is visible in the translucent window 88.

One of the advantages of the present invention is its ability to accommodate needles of various sizes. Depending on the type of automatic injector 50 (and the type of injection for which it is designed), the needle 72 of the automatic injector may range in length from about 0.4 inches (approximately 10 millimeters) to 0.975 inches (approximately 24.8 millimeters). If the needle 72 is sufficiently long, the automatic injector 50 will not be fully seated in the container 10 when the needle 72 strikes the bottom of the container 10. In that case, as the user pushes the automatic injector 50 fully into the container 10, the needle 72 bends and becomes crippled, as shown in FIG. 5B.

Because the bottom 26 of the container 10 and the cover sleeve 84 may be used to cripple the needle, it is advantageous if those components are made of or lined with a tough material that resists penetration, such as PET. Alternatively, a reinforcing plate of either plastic or metal could be fixed to the cover sleeve 84 or the inside bottom 26 of the container 10. Embodiments of the invention that employ a reinforcing component at the bottom of the container will be described below in more detail.

If the user does open the container 10 after the automatic injector 50 has been used, he or she will find it difficult to remove the used automatic injector 50 from the container. This is because the penetrated indicator sleeve 80 acts as a retaining member and exerts a frictional force on the needle 72 that opposes an attempt to remove the automatic injector 50 from the container 10. The indicator sleeve 80, or its bottom portion 81, may be made of a thermoplastic elastomer having a relatively high coefficient of friction so as to produce the greatest possible amount of friction when in engagement with the needle 72. Additionally, if the needle 72 is of a length that causes it to be crippled by striking the bottom 26 of the container 10, the crippled needle 72 itself may make the used automatic injector 50 difficult to remove from the container 10.

Although in the container 10, a cover sleeve 84 is moved by the needle 72 of the automatic injector 50, other embodiments are possible. For example, in another embodiment of the invention that utilizes the same principles as in the container 10, a green indicator flag could be shown through the window 88 until the used automatic injector 50 is inserted into the container 10, at which time the needle 72 of the automatic injector 50 would cause the green indicator flag to be moved to reveal a white or red "used" indicator flag. This could be implemented, for example, by making the cover sleeve 84 green and the underlying indicator sleeve 80 either white or red. Alternatively, a green indicator flag or sleeve could be covered by another movable sleeve. In general, the indicating mechanism and its colors should be chosen so as to give the user a readily identifiable indication of use.

Figure 7:
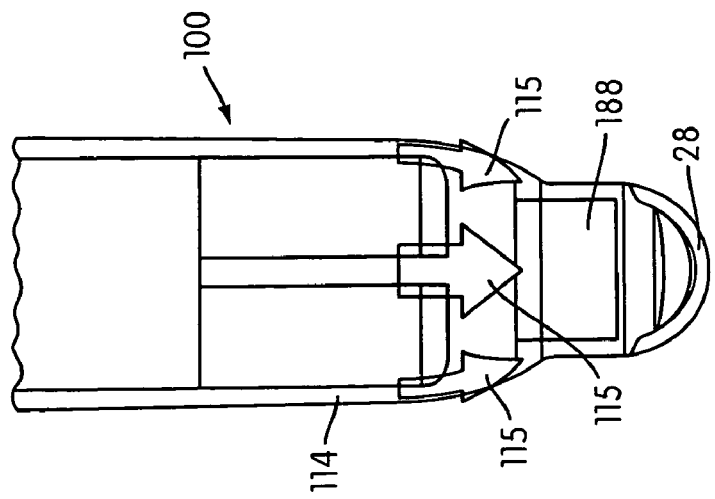
FIG. 7 is a side elevational view of a portion of the exterior of a container according to another embodiment of the present invention.

In the container 10, the visibility of the indicator sleeve 80 through the window 88 provides an indication that the automatic injector 50 has been used. However, in other embodiments of the invention, the needle 72 itself may serve as an indicator that the automatic injector 50 has been used. FIG. 7 is an elevational view of the needle-receiving end 114 of a container 100 according to another embodiment of the invention. The needle-receiving end 114 is sufficiently transparent to allow the needle 72 of the automatic injector 50 to be seen from the outside of the container 100. Therefore, the needle 72 itself acts as an indicator that the automatic injector 50 has been used.

The container 100 has pointing indicia 115 inscribed on the outer surface of the needle-receiving end 114 to direct the user's attention to the portion of the needle-receiving end 114 where the needle 72 is visible when the automatic injector 50 has been used. In alternative embodiments, the pointing indicia 115 may be painted, marked, integrally formed, or applied as labels to the needle-receiving end 114. If desired, the pointing indicia 115 may also be omitted.

Figure 8B:
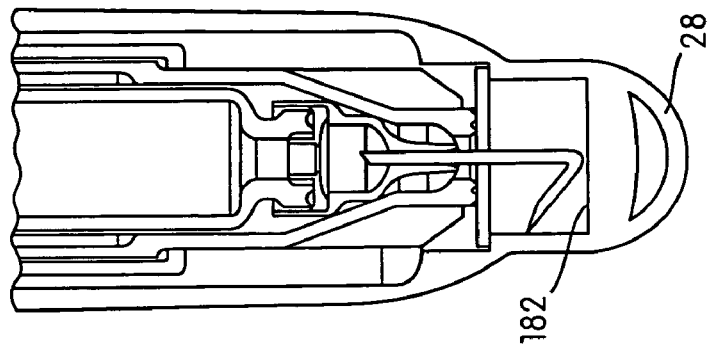
FIG. 8B is a longitudinal cross-sectional view similar to that of FIG. 8A, illustrating the administration end of the automatic injector after the automatic injector has been used and returned to the container.
Figure 8A:
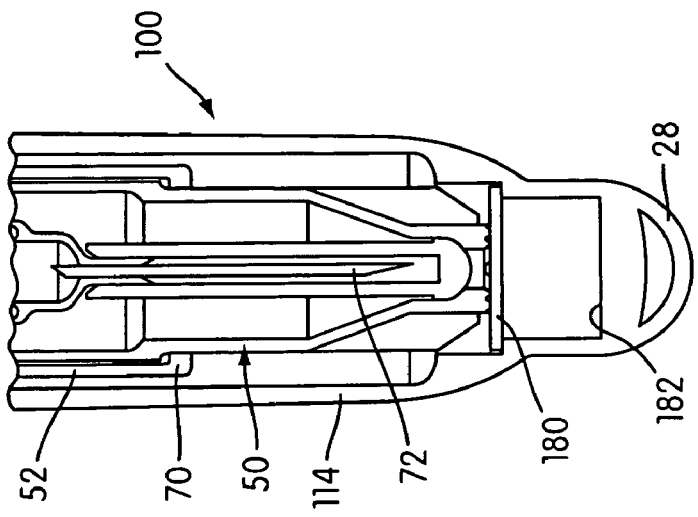
FIG. 8A is a longitudinal cross-sectional view of a portion of the container of FIG. 7, illustrating an unused automatic injector within the container.

FIGS. 8A and 8B are longitudinal cross-sectional views of the portion of the container 100 shown in FIG. 7. In the container 100, the interior mechanism is simpler than in the container 10 of the previous embodiment. FIG. 8A illustrates the position of the automatic injector 50 in the container 100 before activation. The bottom of the automatic injector 50 rests on a needle retainer 180, which is a flexible, resilient component, typically made of a thermoplastic elastomer, that cushions the automatic injector 50 before use.

When the automatic injector 50 is returned to the container 100 after use (optionally by using the container cap 18 to exert greater mechanical advantage on the automatic injector 50), the needle 72 penetrates and advances through the needle retainer 180. The needle 72 can then be seen through a transparent window 188 in the needle-receiving portion 114, indicating that the automatic injector has been used. The needle retainer 180 exerts a frictional force on the needle 72 that tends to oppose an attempt to remove it. If the needle 72 is long enough, it may strike the bottom 182 of the needle-receiving portion 114 and become crippled, as shown in FIG. 8B. The crippled needle 72 may also make the used automatic injector 50 difficult to remove from the container 100. As in the container 10, the bottom 182 of the container 100 would be made of a penetration resistant material, or reinforced with such a material, so as to facilitate needle crippling.

Other embodiments of containers according to the invention may combine the features of the two embodiments described above to provide a colored, highly visible "used" indicator in combination with a simplified container that is designed to retain a used automatic injector. In some embodiments, the indicator function may be provided as a portion of the automatic injector itself.

Figure 9A:
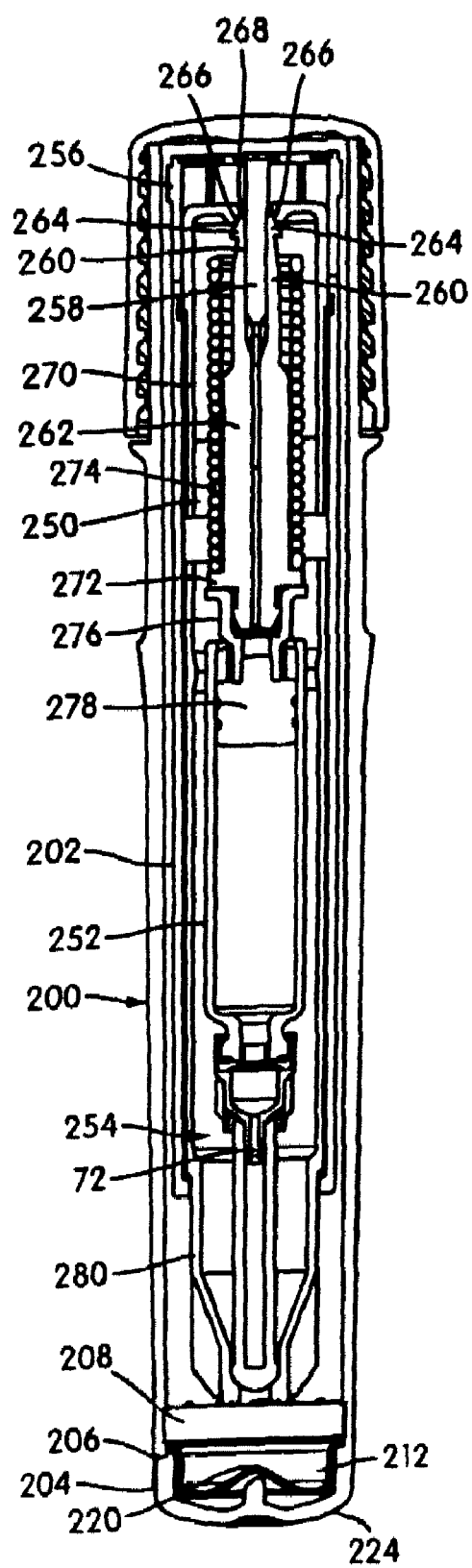
FIG. 9A is a longitudinal cross-sectional view of a container according to another embodiment of the invention with an automatic injector installed therein.
Figure 9B:
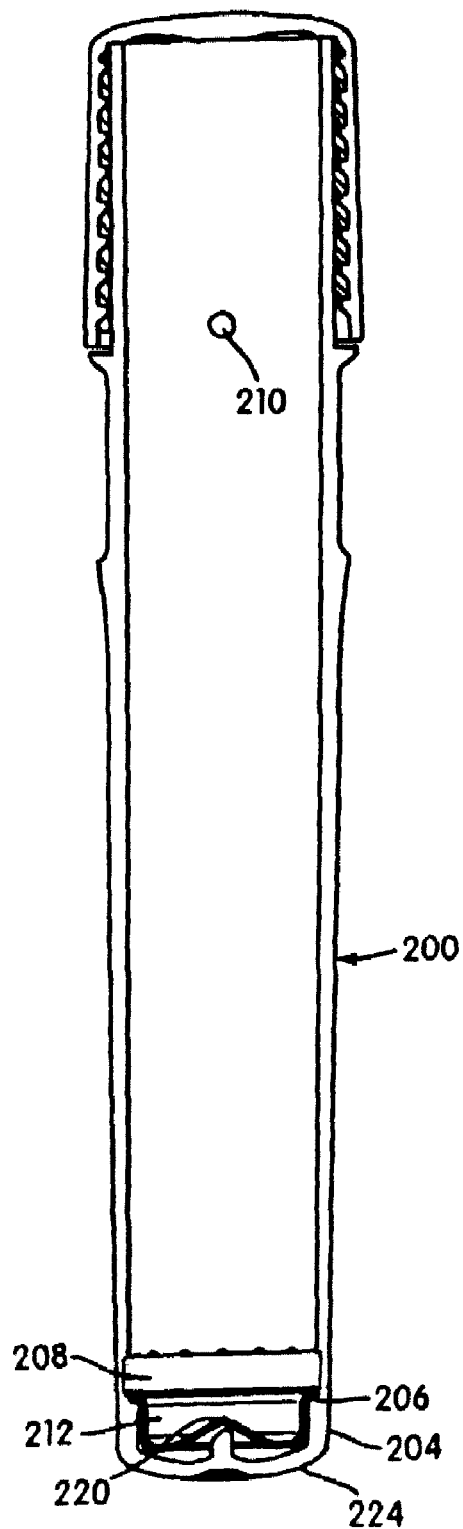
FIG. 9B is a longitudinal cross-sectional view of the container of FIG. 9A without the automatic injector.

For example, FIGS. 9A and 9B are longitudinal cross-sectional views of a container, generally indicated at 200, according to another embodiment of the invention. FIG. 9A shows the container 200 with an exemplary automatic injector 202, also in longitudinal cross-section; FIG. 9B shows the container 200 in longitudinal cross-section without the automatic injector 202.

The container 200 includes many of the features of the containers 10 and 100 that were described above. Certain features that are not shown in FIGS. 9A and 9B, such as an eyelet 28, may also be included in the container 200.

The automatic injector 202 has an actuation assembly, generally indicated at 250, a chamber, generally indicated at 252, that is made of glass, plastic, or another suitable material and is configured to contain a medicament solution, and a hub and needle assembly, generally indicated at 254. However, instead of a single chamber 252 for medicament, the automatic injector 202 may be of the type designed to carry a two component wet/dry medicament or a two component wet/wet medicament, in which case it would have two chambers separated by an appropriate sealing structure. U.S. Pat. Nos. 6,641,561 and 6,770,052 provide details on the construction of such automatic injectors and their sealing and mixing structures.

The actuation assembly 250 includes a safety cap 256 mounted on the rear end of the automatic injector 202. The safety cap 256 includes a downwardly extending safety pin 258 formed on the inward side of the top surface of the cap 256. In the position shown in FIG. 9A, the automatic injector 202 has not been used, the safety cap 256 is on, and the safety pin 258 extends between and engages spring fingers 260 formed in the split rearward portion of a collet 262. The spring fingers 260 each have semi-conical end surfaces 264 that are constructed and arranged to engage corresponding semi-conical surfaces 266 arrayed around an aperture 268 in the rear of the inner housing portion 270 of the automatic injector 202. The engagement of the safety pin 258 with the spring fingers 260 keeps them spread apart and prevents them from deflecting inwardly to enter the aperture 268.

The collet 262 is surrounded by a cylindrical sleeve having an inwardly extending flange at the rearward end thereof. The collet 262 has a forward annular flange 272. A coil spring 274 surrounds the collet 262 and is compressed between the flange of the cylindrical sleeve and the annular flange 272. At its forward end, the collet 262 engages a spacer-indicator member 276.

The spacer-indicator member 276 is a brightly colored component, typically made of red plastic or the equivalent, that includes one end configured to receive and engage the collet 262 and the other end configured to receive and engage a plunger 278 positioned sealingly within the chamber 252 for sliding movement therein. (Alternatively, the spacer-indicator member 276 may engage an insert connected to the plunger 278.) The spacer-indicator member 276 is generally cylindrical in shape, and may be varied in overall length so as to allow the plunger 278 to be initially positioned within the chamber 252 at any desired position. For example, if the medicament dose to be contained in the chamber 252 does not require the entire volume of the chamber 252, the spacer-indicator member 276 may be made with a longer length, so that plunger 278 is initially positioned further along the length of the chamber 252 and the effective volume of the chamber 252 is thus reduced. Therefore, when the volume of the medicament dose is smaller than the volume of the chamber 252, a spacer-indicator member 276 of an appropriate length can reduce the possibility that an air bubble will accumulate in the unused volume of the chamber 252.

To activate the automatic injector 202, the safety cap 256 is manually removed from the automatic injector 202, thus the safety pin 258 is removed from its initial position separating the spring fingers 264. When the forward portion of the housing 280 is pressed against an administration site, the spring fingers 264 are forced upward and, by interaction with the semi-conical surfaces 266, toward one another and off of the retaining surfaces of the flange. The compressed spring 274 is then free to release its stored energy to move the collet 262 forwardly under the force of the spring 274, causing the needle 72 to extend through the forward portion of the housing 280 and the medicament to be injected.

Figure 10A:
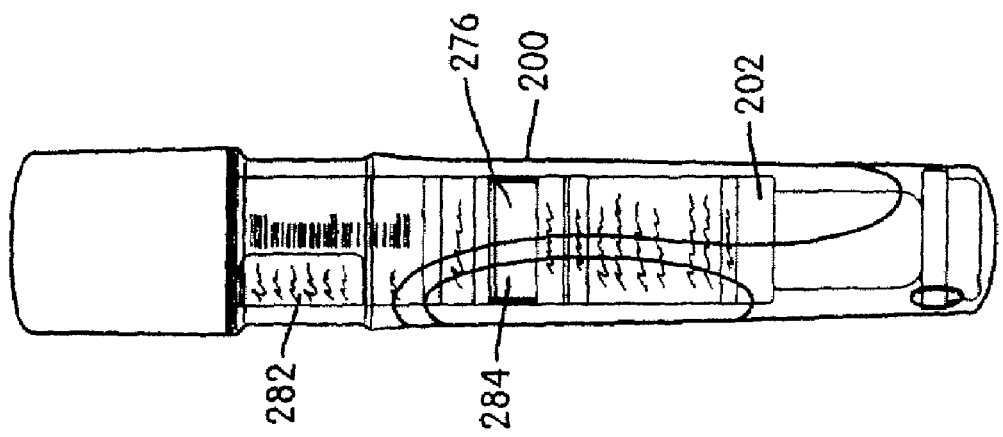
FIGS. 10A and 10B are side elevational views of the container with an automatic injector installed therein before and after use, respectively.
Figure 10B:
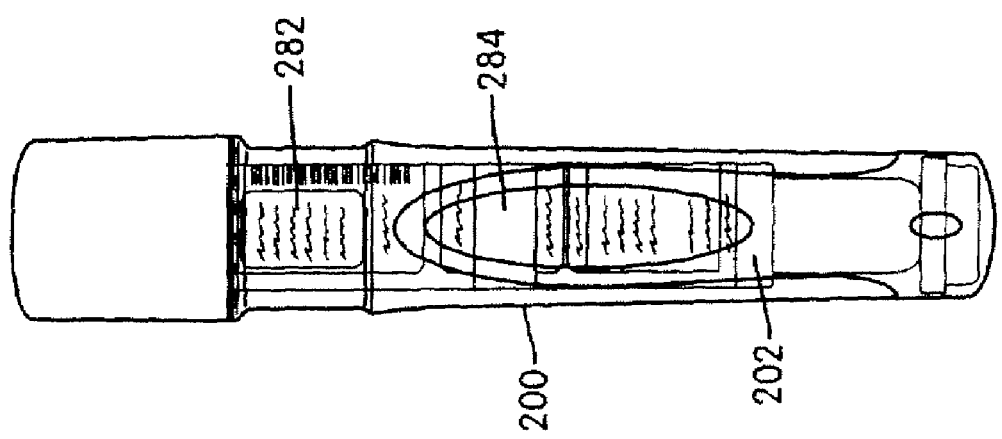

FIGS. 10A and 10B are side elevational views of a container 200 with an automatic injector 202 installed therein before and after use of the automatic injector 202, respectively. As shown in FIGS. 10A and 10B, if a spacer-indicator 276 is used in the automatic injector 202, the container 200 and automatic injector 202 are both preferably made of a material that is at least partially translucent and, more preferably, a material that is at least partially transparent, such as a transparent or substantially transparent plastic. As shown in FIGS. 10A and 10B, labels 282 containing identifying information, patient instructions, and other necessary indicia are placed over portions of the automatic injector 202, leaving a transparent window 284 at a position adjacent to the position into which the spacer-indicator member 276 moves after use of the automatic injector 202. In FIG. 10A, the transparent window 284 is empty and clear. However, in FIG. 10B, the spacer-indicator 276 has moved into the transparent window 284, giving the user a highly visible indication that the automatic injector 202 has been used. In alternative embodiments, portions of the housing of the automatic injector 202 could be made of an opaque plastic and the transparent window 284 could be made of a transparent plastic. The spacer-indicator 276 is generally not configured to be centered in the transparent window 284 once the automatic injector 202 has been used. Rather, as shown in FIG. 10B, it is typically designed to be positioned slightly below center, which provides more visibility at tolerance extremes.

The container 200 has a mechanism for retaining the needle 72 of the automatic injector 202 similar to that of the container 100 illustrated in FIGS. 7, 8A, and 8B. The needle-receiving end 204 of the container 200 has an inner circumferential shelf 206. Resting on the inner circumferential shelf 206 is a needle retainer 208. The needle retainer 208 is slightly larger in diameter than the diameter of the container 200 itself, such that the needle retainer 208 engages the inner walls of the container 200 with an interference fit. Other arrangements are possible; in certain embodiments, the needle retainer 208 may be fused in place, secured with adhesives, snapped in place, or welded in place. The needle retainer 208 is formed of a resilient material and, because of its thickness and resilience, acts as a shock absorber, cushioning the automatic injector 202 before use. The cushioning effect of the needle retainer 208 reduces or eliminates the need for an external structure such as an eyelet 28.

Figure 11:
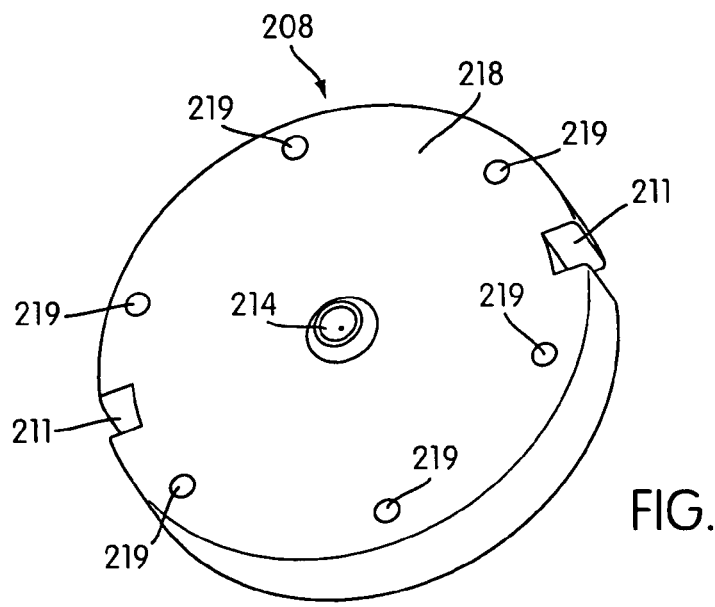
FIG. 11 is a perspective view of a needle retainer that is installed within the container of FIGS. 9A and 9B.
Figure 12:
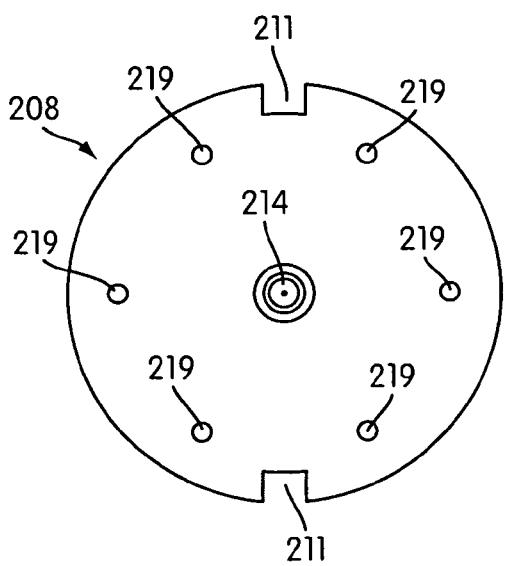
FIG. 12 is a top plan view of the needle retainer of FIG. 11.
Figure 13:
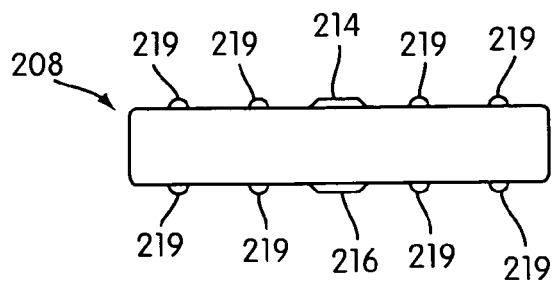
FIG. 13 is a side elevational view of the needle retainer of FIG. 11.

FIGS. 11, 12, and 13 are perspective, top plan, and side elevational views, respectively, of the needle retainer 208. As shown, the needle retainer 208 is substantially circular. The needle retainer 208 includes two vent slots 211 spaced 180° from each other along the circumference of the needle retainer 208. The vent slots 211 ensure that pressure does not build up on one side of the needle retainer 208 and enable any gases or vapors to move out of the container 200. (The container 200 also has a vent hole 210, which is shown in FIG. 9B.) In the center of the upper surface of the needle retainer 208 is a raised central portion 214. A similar raised central portion 216 is provided on the bottom surface, as shown in FIG. 13. The raised central portions 214, 216 provide the needle retainer 208 with a greater effective thickness in the area through which the needle 72 will be inserted, thereby improving the frictional "grip" of the needle retainer 208 on the needle 72 and also aid gating of the tool during the manufacturing process. In addition to the raised central portions 214, 216, the needle retainer 208 also includes a number of protuberances 219 spaced regularly around its circumference. The protuberances 219 improve the manufacturability of the container 200 and its assembly process by making it easier to separate stacked needle retainers 208 during manufacturing and assembly. However, needle retainers 208 may be made without the raised central portions 214, 216 and the protuberances 219.

Below the needle retainer 208 in the needle-receiving end 204 of the container 200 is a shield 212 which is held in place both by engagement with the inner circumferential shelf 206 and by the fit of the needle retainer 208 above it. The shield 212 is substantially cap-shaped and rests on the bottom of the needle-receiving end 204 of the container with its open end facing upwards. In general, the shield 212 is intended to prevent the needle 72 from penetrating the container 200. Typically, the shield 212 would be made of stainless steel or another metal that is compatible with (i.e., not corroded or otherwise damaged by) the medicament in the automatic injector 202. However, in some embodiments, the shield 212 may be made of PET or another penetration resistant plastic.

Figure 14:
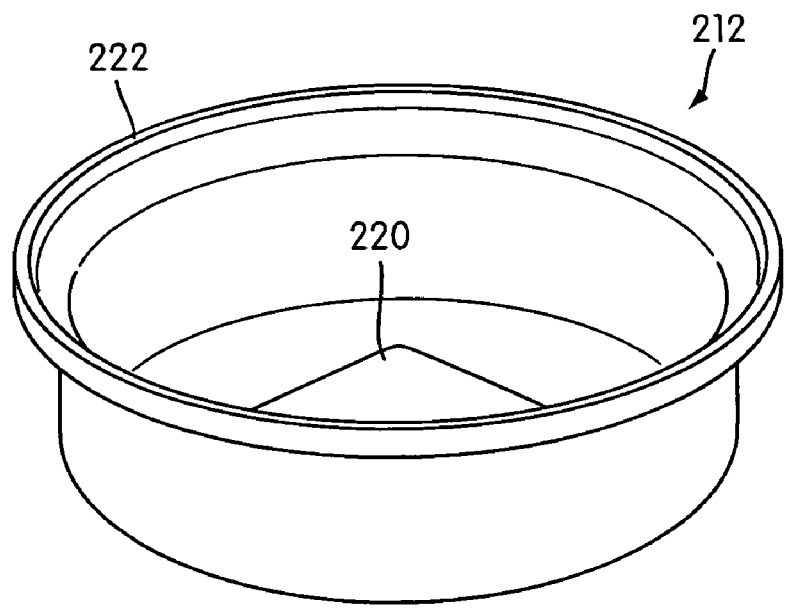
FIG. 14 is an isolated perspective view of a shield that is installed within the container of FIGS. 9A and 9B.
Figure 15:
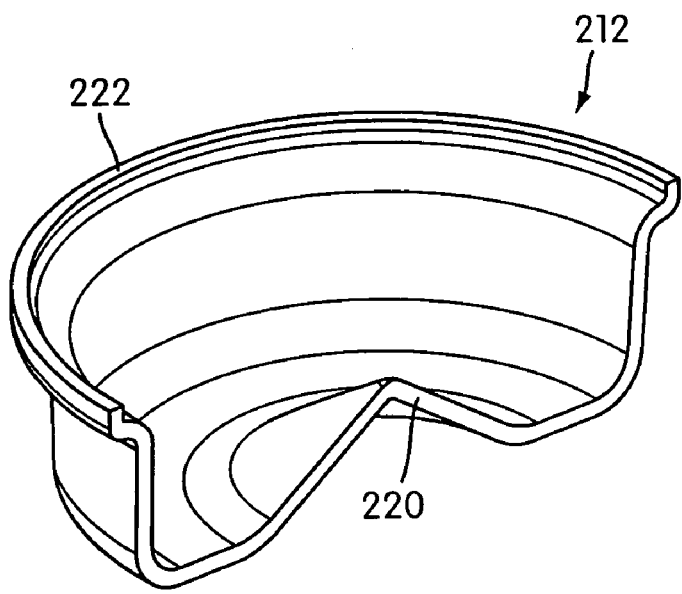
FIG. 15 is a sectional perspective view of the shield of FIG. 14.

FIG. 14 is a perspective view of the shield 212 in isolation, and FIG. 15 is a sectional perspective view of the shield 212 in isolation. As shown in FIGS. 14 and 15, in the center of the shield 212 is an upwardly extending conical portion 220. The conical portion 220 increases the possibility that a shorter needle will be crippled after insertion into the container 200. In general, the upwardly extending conical portion 220 also reduces the amount of force necessary to deflect and cripple the needle 72. Of course, the shield 212 need not include a conical projection 220 per se; an upward projection of the shield 212, if provided, could have substantially any shape.

Figure 16:
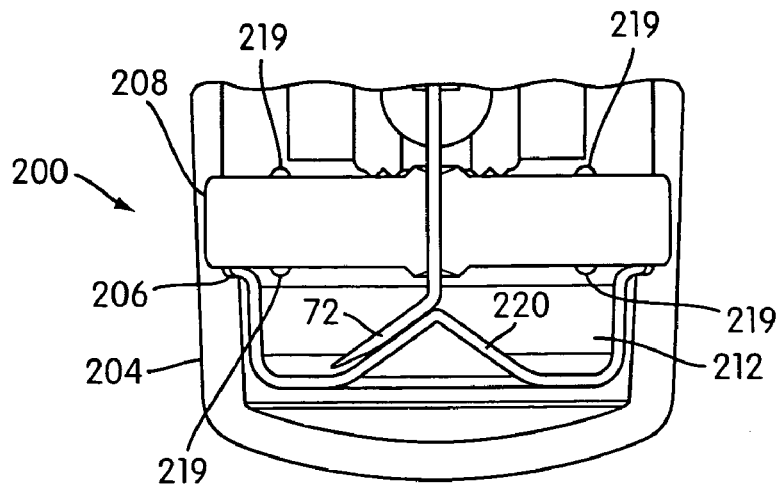
FIG. 16 is a sectional side elevational view of a portion of the container of FIGS. 9A and 9B with an automatic injector installed therein after use of the automatic injector, illustrating the needle of the automatic injector in a crippled position.

If the needle 72 is of sufficient length to strike the shield 212 and become crippled, its final position after contact with the shield 212 may be that shown in FIG. 16, a sectional side elevational view of a portion of the needle-receiving end 204 of the container 200. As shown in FIGS. 14-16, in addition to the conical portion 220, the shield 212 also includes an upwardly extending flange 222 that helps to prevent any portion of the crippled, deformed needle 72 from escaping the area enclosed by the shield 212 and the needle retainer 208.

To some extent, the spacing between the needle retainer 208 and the shield 212 adds to the cushioning and shock absorbing effect of the needle retainer 208, because the needle retainer 208 can deflect and rebound to dissipate shock.

In the embodiment of FIGS. 9A and 9B, the container 200 includes a central upward projection 224 that extends upwardly from the bottom of the container 200 and coincides in position with the conical portion 220 of the shield 212. The projection 224 may be used to center the shield 212 when the shield is inserted into the container 200, and it may also reinforce the conical portion 220, particularly if the conical portion 220 deflects downwardly in response to initial contact with the needle 72. In the alternative embodiment depicted in FIG. 16, the projection 224 is not provided.

Figure 17:
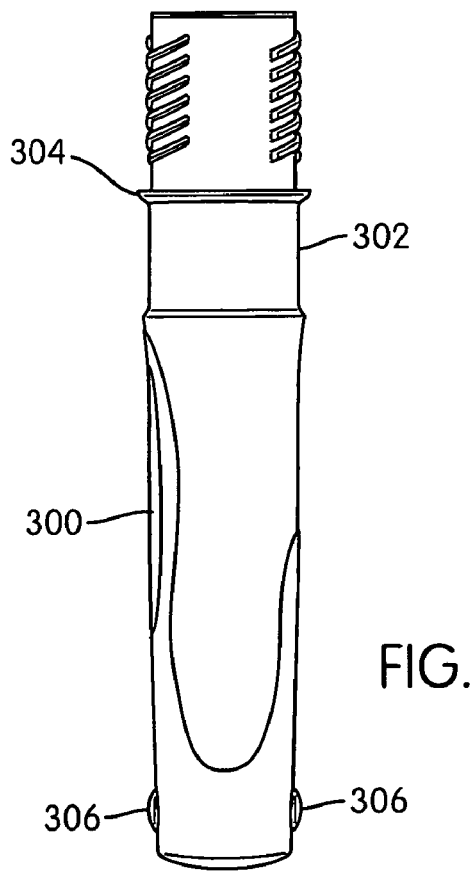
FIG. 17 is a side elevational view of the exterior of the container of FIGS. 9A and 9B.

FIG. 17 is a side elevational view of the exterior of the container 200. The exterior of the container 200 also includes certain advantageous features. For example, a frosted grip area 300 increases the tactility of the surface and encourages a firm grip. A smooth recessed surface 302 provides a location for a clip or other such retaining device to be attached around the circumference of the container 200. The recessed surface 302 is also preferably transparent and may be used as a window so that users and treating medical professionals can determine whether the automatic injector 202 is in the container 200 and, if so, what drug it contains. Typically, labels on the automatic injector 202 describing its medicament would be placed so as to coincide with the position of the recessed surface 302. Because the surface 302 is recessed, it is less likely to become scratched and obscure the interior of the container 200. Additionally, labels on the automatic injector 202 may be visible through portions of the container 200 other than the frosted grip area 300.

A flange 304 on the upper portion of the container 200 defines the position to which the user will need to screw the cap 18 in order to ensure that the needle 72 is crippled after it enters the container 200. (Typically, the arrangement of the container 200 and the cap 18 is such that a small vent gap is left between the two when the cap 18 is screwed down fully.)

The container 200 also includes two anti-roll protrusions 306 spaced opposite one another on the lower portion of the outer surface of the container 200. The anti-roll protrusions 306 reduce the likelihood that the container 200 will roll more than about 180° from the position in which it is placed. Although the container 200 does not include an eyelet 28, its bottom surface 308 is rounded, which helps to dissipate shock if the container 200 is dropped on its end.

As was described above, the recessed surface 302 provides a surface over which a clip may be placed to attach multiple containers 200 to one another. Such clips may be used on other containers 10, 100 according to the invention, although the recessed surface 302 substantially prevents a clip from sliding along the length of the container 200.

Figure 18:
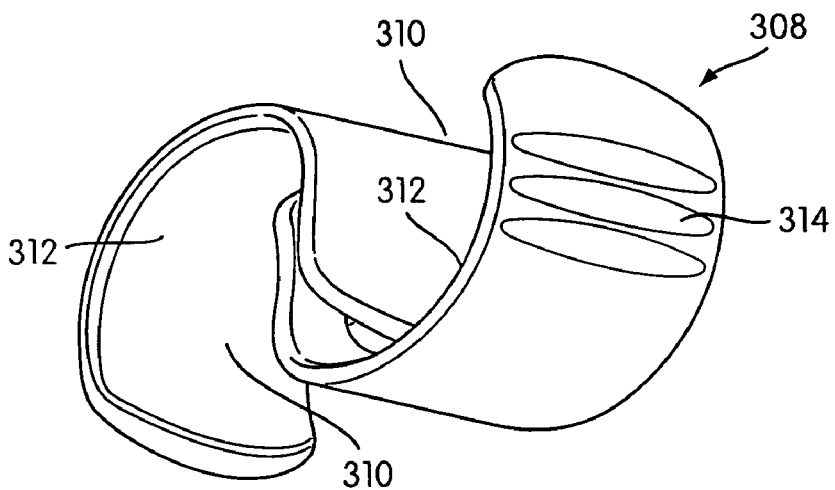
FIG. 18 is a perspective view of an S-clip that may be used to attach two containers according to the invention.
Figures 19, 20:
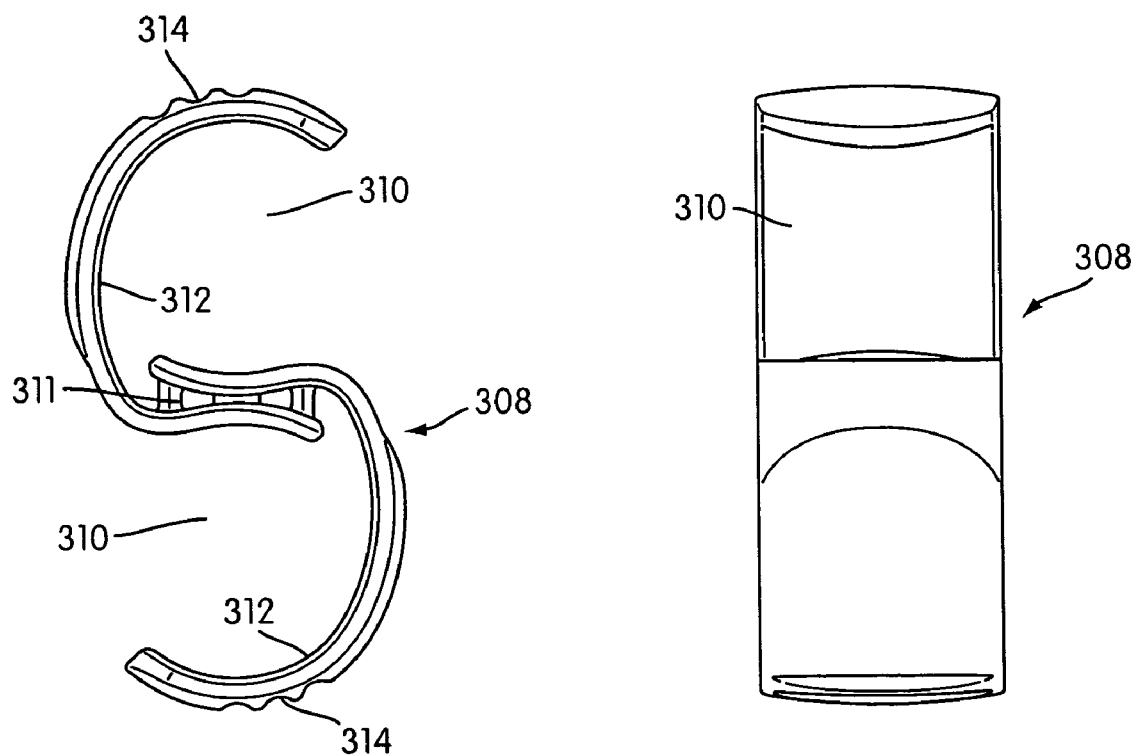
FIG. 19 is a top plan view of the S-clip of FIG. 18.
FIG. 20 is a side elevational view of the S-clip of FIG. 18.

FIG. 18 is a perspective view of an S-clip, generally indicated at 308, that may be used with containers 10, 100, 200 according to the invention. FIGS. 19 and 20 are, respectively, a top plan view and a side elevational view of the clip 308. The clip 308 is contoured such that it has two clip openings 310, with each clip opening 310 configured to accept one container 10, 200, 300. The two clip openings 310 are opposite one another, and the portions of the clip 308 that define each opening 310 are joined by a central web of material 311. The clip 308 may be formed from any suitable material that permits the clip to 308 to flex and engage the side of the container 10, 200, 300.

As is best seen in FIG. 19, the engaging surfaces 312 that define the interior of each of the clip openings 310 have a different radius of curvature than that of the containers 10, 200, 300. The different radius of curvature of the engaging surfaces 312 and the containers 10, 200, 300 allows the clip 308 to engage a container with minimal contact between the engaging surfaces 312 and the container 10, 100, 200. Minimal contact between the engaging surfaces 312 and the container 200 reduces the likelihood that the engaging surfaces 312 of the clip 308 will scratch the transparent recessed surface 302 of the container 200.

The overall "S" shape of the clip 308 will reduce the amount of force needed to remove a container 10, 100, 200 from the clip 308 in an emergency, as compared with a more conventional double C-clip. Additionally, texture 314 on the outer surface of the clip 308 makes the clip 308 easier to grip and may encourage users to replace the container 10, 100, 200 in the clip 308 once the automatic injector 50, 202 has been used. It is contemplated that the clip 308 may include a suitable attachment assembly for carrying the clip on a belt or securing to an article of clothing or desired surface or article.

Although the invention has been described with respect to certain embodiments, the described embodiments are intended to be exemplary, rather than limiting. Modifications and variations to those embodiments are possible within the scope of the appended claims.

What is claimed is:

1. An automatic injector package, comprising:
  an automatic injector including:
    a housing;
    a cartridge assembly located in said housing;
    a needle assembly operatively associated with said cartridge assembly; and
    an actuation assembly located in said housing, said actuation assembly including a stored energy source and a drive assembly driven by said stored energy source, said drive assembly being operatively associated with said cartridge assembly and said needle assembly to expel a medicament from the cartridge and through said needle assembly upon activation of the automatic injector;

a container constructed and arranged to completely enclose the automatic injector within the container before and after use of the automatic injector, the automatic injector requiring removal from the container in order to be used and having an exposed needle after said use, the exposed needle becoming bent and crippled upon the automatic injector's return to the container after said use, said container having at least a portion thereof formed from a light permeable material; and indicia provided on at least one of said housing and said container, said indicia being visible by a user when the automatic injector has been placed into said container after use, said indicia pointing to an indicating portion that indicates that the automatic injector has been used.

2. The automatic injector package of claim 1, wherein said indicating portion comprises an exposed needle visible through said container.

3. The automatic injector package of claim 1, wherein said indicating portion comprises a movable sleeve carried by the container that is moved to an indicating position by the automatic injector needle when the used injector is inserted into the container.

4. The automatic injector package of claim 1, wherein said housing is made from a light permeable material, and wherein said indicating portion is a member within the housing.

5. The automatic injector package of claim 4, wherein said member is a spacer that is moved to an indicating position within said housing after activation of the automatic injector.

6. The automatic injector package of claim 5, wherein said spacer is provided in said drive assembly.

7. The automatic injector package of claim 5, wherein said spacer is brightly colored.

8. The automatic injector package of claim 1, further comprising a needle engaging retaining structure disposed within the container for retaining the automatic injector in said container by engaging an exposed needle of said automatic injector after use.

9. The automatic injector package of claim 8, wherein said needle engaging retaining structure comprises a resilient member.

10. An automatic injector package comprising:
an automatic injector including:
a housing;
a cartridge assembly located in said housing;
a needle assembly operatively associated with said cartridge assembly; and
an actuation assembly located in said housing, said actuation assembly including a stored energy source and a drive assembly driven by said stored energy source, said drive assembly being operatively associated with said cartridge assembly and said needle assembly to expel a medicament from the cartridge and through said needle assembly upon activation of the automatic injector;

a container constructed and arranged to receive the automatic injector therein before and after use, the automatic injector having an exposed needle after said use, said container having at least a portion thereof formed from a light permeable material, the container comprising a needle retainer disposed within the container for retaining the automatic injector in said container by engaging an exposed needle of said automatic injector after use, said needle retainer comprising a resilient member and raised central portions on top and bottom surfaces thereof; and indicia provided on at least one of said housing and said container, said indicia being visible by a user when the automatic injector has been placed into said container after use, said indicia pointing to an indicating portion that indicates that the automatic injector has been used.

11. The automatic injector package of claim 10, wherein said needle retainer includes a downwardly-extending guide surface in the top raised central portion.

12. The automatic injector package of claim 11, wherein the needle retainer includes a number of protuberances on top and bottom surfaces thereof.

13. The automatic injector package of claim 1, wherein the automatic injector container further comprises a shield disposed in a bottom portion of the container.

14. The automatic injector package of claim 13, wherein the shield further comprises an upwardly extending portion.

15. The automatic injector package of claim 14, wherein said upwardly extending portion is an upwardly extending substantially conical portion.

16. The automatic injector package of claim 13, wherein the shield further comprises a flange portion adapted to prevent the needle from escaping an area of the container body enclosed by the shield.

17. The automatic injector package of claim 1, further comprising a cap constructed and arranged to engage an open end of said container body so as to be in closed relation therewith.

18. The automatic injector package of claim 1, wherein the container body is longer than a length of the automatic injector with the needle of the cartridge and needle assembly in an extended position.

19. A container for receiving therein an automatic injector, the container comprising:
an open end;
one or more interior walls forming a hollow interior sized and configured to receive an automatic injector through the open end;
a closed end opposite the open end;
a cap constructed and arranged to releasably engage the open end so as to releasably close the open end, wherein the interior walls, the closed end, and the cap releasably engaging, the open end completely enclose an automatic injector within the hollow interior between the cap and the closed end;
a needle retainer mounted within the container proximate the closed end; and
a shield mounted within the container between the needle retainer and the closed end of the container, the shield operative to prevent penetration there through by an exposed needle of an automatic injector.

20. The container of claim 19, wherein the shield is formed of a penetration resistant plastic.

21. The container of claim 19, wherein the shield further comprises an upwardly extending portion.

22. The container of claim 21, wherein said upwardly extending portion is an upwardly extending substantially conical portion.

23. The container of claim 19, wherein the shield is formed of a metal.

24. The container of claim 19, wherein the container is formed of a light permeable material.

25. The container of claim 19, further comprising
an indicator sleeve mounted within a portion of the container, a lower portion of the indicator sleeve comprising the needle retainer; and
a cover sleeve movably mounted between the indicator sleeve and walls of the container, a needle-contacting surface of the cover sleeve extending below the lower needle retainer portion of the indicator sleeve;
wherein when the automatic injector is replaced in the container, the extended needle of the automatic injector advances through the lower needle retainer portion of the indicator sleeve, contacts the needle-contacting surface of the cover sleeve, and forces the cover sleeve to move, thereby making the indicator sleeve visible through the container.

26. The container of claim 19, wherein the closed end of the container is outwardly rounded.

27. The container of claim 26, further comprising an eyelet disposed over the closed end of the container, the eyelet covering at least 20% of the closed end.

28. The container of claim 19, further comprising anti-roll protrusions provided on an exterior surface thereof.

29. The container of claim 19, further comprising a flange provided proximate to the open end of the container at a location corresponding to the fully engaged position of the cap.

30. The container of claim 19, further comprising a vent opening in the container.

31. The container of claim 19, wherein the needle retainer includes one or more vents.

32. The container of claim 19, further comprising a recessed portion on an exterior surface thereof.

33. A method of constructing a container for carrying and storing an automatic injector before and after use of the injector, the method comprising:
forming an elongated body having an open end and a closed end opposite the open end, the elongated body having one or more interior walls forming a hollow interior sized and configured to receive an automatic injector through the open end;
forming a cap sized and configured to engage the open end to open and close the open end, wherein the interior walls, the closed end, and the cap closing the open end completely enclose an automatic injector within the hollow interior between the cap and the closed end;
forming a retainer sized to fit within and laterally across the hollow interior;
forming the retainer from a resilient material operative to cushion an automatic injector stored within the hollow interior prior to use of the automatic injector and to receive and retain there through an exposed needle of the automatic injector after use of the automatic injector;
engaging the retainer with the one or more interior walls proximate the closed end; and
mounting a shield within the container between the retainer and the closed end of the container, the shield operative to prevent penetration there through by an exposed needle of an automatic injector.

34. A container for receiving therein an automatic injector, the container comprising:
an open end;
one or more interior walls forming a hollow interior sized and configured to receive an automatic injector through the open end;
a closed end opposite the open end;
a cap constructed and arranged to releasably engage the open end so as to releasably close the open end, wherein the interior walls, the closed end, and the cap releasably closing the open end completely enclose the automatic injector within the hollow interior between the cap and the closed end; and
a needle retainer mounted within the container proximate the closed end but not contacting the closed end, the needle retainer formed of a resilient material operative to cushion an automatic injector stored within the container prior to use of the automatic injector and to retain an exposed needle of the automatic injector after use of the automatic injector when penetrated by the exposed needle,
wherein: the exposed needle becomes bent and crippled upon the automatic injector's return to the container after said use.

35. The container of claim 34, further comprising a penetration resistant shield positioned between the needle retainer and the closed end of the container.

36. A container for receiving therein an automatic injector, the container comprising:
an open end;
one or more interior walls forming a hollow interior sized and configured to receive an automatic injector through the open end;
a closed end opposite the open end;
a car constructed and arranged to releasably engage the open end so as to releasably close the open end, wherein the interior walls, the closed end, and the cap releasably closing the open end completely enclose the automatic injector within the hollow interior between the cap and the closed end; and
a needle retainer mounted within the container proximate the closed end but not contacting the closed end, the needle retainer formed of a resilient material operative to cushion an automatic injector stored within the container prior to use of the automatic injector and to retain an exposed needle of the automatic injector after use of the automatic injector when penetrated by the exposed needle, wherein
the exposed needle becomes bent and crippled upon the automatic injector's return to the container after said use: the container further comprising;
a clip constructed and arranged to attach to an exterior surface of the container.

37. The container of claim 36, wherein the clip is an S-clip.

38. The container of claim 36, wherein engaging surfaces of the clip have a radius of curvature different from a radius of curvature of the exterior surface of the container.

39. The container of claim 37, wherein the S-clip is configured to receive a pair of containers.

40. The container of claim 38, wherein the S-clip includes engaging surfaces, one of the engaging surfaces engaging one of the containers and another of the engaging surfaces engaging another of the containers, each engaging surface of the clip having a radius of curvature different from a radius of curvature of the exterior surface of the container.

41. The method of claim 33, further comprising forming one or more vents through the retainer.

42. The method of claim 33, further comprising:
forming an inner circumferential shelf in the hollow interior proximate the closed end; and
resting the retainer on the circumferential shelf.

43. The method of claim 33, further comprising forming a raised central portion on the retainer.

44. A method of constructing a container for carrying and storing an automatic injector before and after use of the injector, the method comprising:

forming an elongated body having an open end and a closed end opposite the open end, the elongated body having one or more interior walls forming a hollow interior sized and configured to receive an automatic injector completely therein through the open end;

forming a cap sized and configured to engage the open end to open and close the open end;

forming a retainer sized to fit within and laterally across the hollow interior;

forming the retainer from a resilient material operative to cushion an automatic injector stored within the hollow interior prior to use of the automatic injector and to receive and retain there through an exposed needle of the automatic injector after use of the automatic injector;

forming a plurality of protuberances on the retainer; and engaging the retainer with the one or more interior walls proximate the closed end.

45. The method of claim 33, further comprising:

forming the shield from a needle-penetration resistant material.

46. The method of claim 33, further comprising:

forming the shield with a central projecting portion; and inserting the shield in the hollow interior positioned between the closed end and the retainer such that the central projecting portion points to the retainer.

47. The method of claim 33, further comprising forming a central projection extending into the hollow interior from the closed end of the container.

48. The method of claim 33, further comprising forming a transparent portion in the elongated body of the container.

49. The method of claim 33, wherein the engaging the retainer comprises engaging the retainer with the one or more interior walls proximate the closed end with an interference fit.

50. The method of claim 33, wherein the engaging the retainer comprises engaging the retainer with the one or more interior walls proximate the closed end with an adhesive.

* * * * *

UNITED STATES PATENT AND TRADEMARK OFFICE
CERTIFICATE OF CORRECTION

PATENT NO. : 7,635,348 B2
APPLICATION NO. : 10/978827
DATED : December 22, 2009
INVENTOR(S) : Raven et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 731 days.

Signed and Sealed this

Ninth Day of November, 2010

David J. Kappos
*Director of the United States Patent and Trademark Office*